US009675536B2

(12) United States Patent
Sakamoto et al.

(10) Patent No.: US 9,675,536 B2
(45) Date of Patent: Jun. 13, 2017

(54) GEL-LIKE COMPOSITION FOR COSMETIC PREPARATIONS

(71) Applicant: ADEKA CORPORATION, Tokyo (JP)

(72) Inventors: Takao Sakamoto, Tokyo (JP); Yasuhiro Tsushima, Tokyo (JP)

(73) Assignee: ADEKA CORPORATION, Tokyo (JP)

( * ) Notice: Subject to any disclaimer, the term of this patent is extended or adjusted under 35 U.S.C. 154(b) by 0 days.

(21) Appl. No.: 14/895,948

(22) PCT Filed: Jun. 5, 2014

(86) PCT No.: PCT/JP2014/064969
§ 371 (c)(1),
(2) Date: Dec. 4, 2015

(87) PCT Pub. No.: WO2014/196600
PCT Pub. Date: Dec. 11, 2014

(65) Prior Publication Data
US 2016/0120779 A1    May 5, 2016

(30) Foreign Application Priority Data
Jun. 7, 2013    (JP) .................................. 2013-120963

(51) Int. Cl.
| | | |
|---|---|---|
| A61K 8/42 | (2006.01) |
| A61K 8/86 | (2006.01) |
| A61K 8/34 | (2006.01) |
| A61K 8/04 | (2006.01) |
| A61Q 19/00 | (2006.01) |
| A61K 8/87 | (2006.01) |

(52) U.S. Cl.
CPC .............. *A61K 8/42* (2013.01); *A61K 8/042* (2013.01); *A61K 8/342* (2013.01); *A61K 8/86* (2013.01); *A61K 8/87* (2013.01); *A61Q 19/00* (2013.01); *A61K 2800/10* (2013.01); *A61K 2800/48* (2013.01); *A61K 2800/592* (2013.01)

(58) Field of Classification Search
None
See application file for complete search history.

(56) References Cited

U.S. PATENT DOCUMENTS

| | | | |
|---|---|---|---|
| 6,440,431 B1* | 8/2002 | Yoshida ................... | A61K 8/86 |
| | | | 424/401 |
| 2003/0012761 A1 | 1/2003 | Yoshida et al. | |
| 2013/0156831 A1 | 6/2013 | Matsuo et al. | |

FOREIGN PATENT DOCUMENTS

| | | |
|---|---|---|
| JP | 2000-239120 | 9/2000 |
| JP | 2000-239649 | 9/2000 |
| JP | 2009-280656 | 12/2009 |
| WO | 2007/145399 | 12/2007 |
| WO | 2011/136270 | 11/2011 |

OTHER PUBLICATIONS

International Search Report issued Sep. 9, 2014 in International Application No. PCT/JP2014/064969.
Extended European Search Report issued Feb. 13, 2017 in corresponding European Application No. 14806855.4.

* cited by examiner

*Primary Examiner* — Dennis Heyer
(74) *Attorney, Agent, or Firm* — Wenderoth, Lind & Ponack, L.L.P.

(57) ABSTRACT

The present invention relates to a gel-like composition for a cosmetic preparation including 0.05 part by mass to 3 parts by mass of a compound represented by the following general formula (1) with respect to 100 parts by mass of water, which is not destroyed by a change in pH or by the addition of a salt into the gel, and gives a feeling of use equivalent to that of a gel produced using an alkali thickening type gelling agent.

$$R^1-O-(C_2H_4O)_m-\overset{O}{\underset{\|}{C}}-\overset{H}{\underset{|}{N}}-R^3-\overset{H}{\underset{|}{N}}-\overset{O}{\underset{\|}{C}}-\left[O-(C_2H_4O)_x-\overset{O}{\underset{\|}{C}}-\overset{H}{\underset{|}{N}}-R^4-\overset{H}{\underset{|}{N}}-\overset{O}{\underset{\|}{C}}\right]_y(OC_2H_4)_n-O-R^2 \quad (1)$$

where, $R^1$ and $R^2$ each represent an alkyl group having 28 to 36 carbon atoms, $R^3$ and $R^4$ each represent a hydrocarbon group having 4 to 13 carbon atoms, m and n each represent a number from 10 to 500, x represents a number from 1 to 1,000, and y represents a number from 0 to 10.

10 Claims, No Drawings

GEL-LIKE COMPOSITION FOR COSMETIC PREPARATIONS

TECHNICAL FIELD

The present invention relates to a gel-like composition that has a viscous property optimum for a cosmetic preparation, has high stability, and is soluble in water.

BACKGROUND ART

Water-based gel-like substances are used in various fields such as paints, adhesives, foods, and cosmetic preparations. Each of such gel-like substances is prepared by adding a gelling agent to water or an emulsion or the like, and in general, desired gel properties vary depending on fields or applications where the substances are used. For example, in the paint field, the substances are used for preventing drippage after paint application or for preventing separation of paint components to improve preservation stability, and in the food field, the substances are used for maintaining the shape of a low-viscosity product such as a cream or for improving a preservation state of a product. In such fields, the products are produced as gel-like substances to achieve effects provided by increasing the viscosities of the products. However, it is important that cosmetic preparations provide not only such effects but also an effect that is not required in other fields, i.e., a feeling given by adhering or applying the products to the skin or the like of a human body.

As gelling agents for preparing the gel-like substances, there are known: a natural gelling agent such as carboxymethylcellulose, hydroxyethylcellulose, or carrageenan; an alkali thickening type gelling agent such as polyacrylic acid or a polyacrylate-containing copolymer; and a urethane-based gelling agent such as urethane-modified polyether (see, for example, Patent Literature 1 to 3). Of the gelling agents, the alkali thickening type gelling agent is preferably used for a cosmetic preparation. This is because a gel prepared by using the alkali thickening type gelling agent provides smooth texture and natural feeling of use and hence gives a favorable feeling of use to many people.

CITATION LIST

Patent Literature

[PTL 1] JP 11-246353 A
[PTL 2] JP 2008-308452 A
[PTL 3] JP 2000-239120 A

SUMMARY OF INVENTION

Technical Problem

However, a gel prepared by using the alkali thickening type gelling agent is destroyed by a change in pH or by the addition of a salt into the gel. This is because the alkali thickening type gelling agent has a structure of a salt form and is easily affected by pH or by another salt. Therefore, there has been a problem in that the gel produced using the alkali thickening type gelling agent can be used only for specific cosmetic preparations.

Therefore, a problem to be solved by the present invention is to provide a gel that is not destroyed by a change in pH or by addition of a salt into the gel and gives a feeling of use equivalent to that of a gel produced using an alkali thickening type gelling agent.

Solution to Problem

Accordingly, the inventors of the present invention have keenly investigated and have found a specific urethane compound, to complete the present invention. That is, according to one embodiment of the present invention, there is provided a gel-like composition for a cosmetic preparation comprising 0.05 part by mass to 3 parts by mass of a compound represented by the following general formula (1) with respect to 100 parts by mass of water.

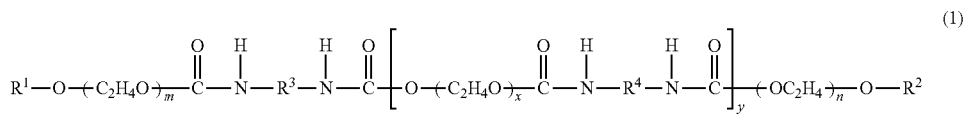

(1)

(Where, $R^1$ and $R^2$ each represent an alkyl group having 28 to 36 carbon atoms, $R^3$ and $R^4$ each represent a hydrocarbon group having 4 to 13 carbon atoms, m and n each represent a number from 10 to 500, x represents a number from 1 to 1,000, and y represents a number from 0 to 10.)

Advantageous Effects of Invention

The effect of the present invention is to provide the gel which is not destroyed by a change in pH or by the addition of a salt into the gel and which gives a feeling of use equivalent to that of a gel prepared by using an alkali thickening type gelling agent.

DESCRIPTION OF EMBODIMENTS

A compound represented by general formula (1) to be used in the present invention is represented by the following structural formula.

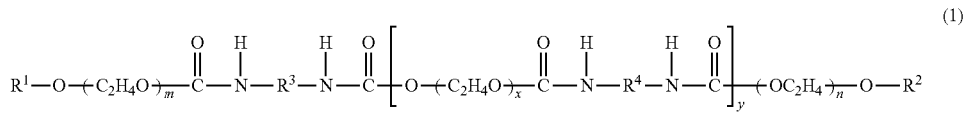

(1)

(where, $R^1$ and $R^2$ each represent an alkyl group having 28 to 36 carbon atoms, $R^3$ and $R^4$ each represent a hydrocarbon group having 4 to 13 carbon atoms, m and n each represent a number from 10 to 500, x represents a number from 1 to 1,000, and y represents a number from 0 to 10.)

$R^1$ and $R^2$ in general formula (1) each represent an alkyl group having 28 to 36 carbon atoms. Examples of such alkyl group include: linear alkyl groups such as an octacosyl group, a nonacosyl group, a triacontyl group, a hentriacontyl group, a dotriacontyl group, a tritriacontyl group, a tetratriacontyl group, a pentatriacontyl group, and a hexatriacontyl group; and branched alkyl groups such as an isooctacosyl group, an isononacosyl group, an isotriacontyl group, an isohentriacontyl group, an isodotriacontyl group, an isotritriacontyl group, an isotetratriacontyl group, an isopentatriacontyl group, an isohexatriacontyl group, a 2-dodecylhexadecyl group, a 2-tetradecylhexadecyl group, a 2-tetradecyloctadecyl group, a 2-hexadecyloctadecyl group, and a 2-hexadecyleicosyl group. Of those, from the viewpoint of a satisfactory feeling of use, branched alkyl groups are preferred, 2-position branched alkyl groups (such as a 2-dodecylhexadecyl group, a 2-tetradecylhexadecyl group, a 2-tetradecyloctadecyl group, a 2-hexadecyloctadecyl group, and a 2-hexadecyleicosyl group) are more preferred, 2-position branched alkyl groups each having 32 carbon atoms are still more preferred, and a 2-tetradecyloctadecyl group is even more preferred. A satisfactory feeling of use cannot be obtained if the group has less than 28 carbon atoms, and availability of a raw material for the compound becomes poor if the group has more than 36 carbon atoms.

$R^3$ and $R^4$ in general formula (1) each represent a hydrocarbon group having 4 to 13 carbon atoms. Examples of such hydrocarbon include a butylene group, a pentylene group, a hexylene group, a heptylene group, an octylene group, a nonylene group, a decylene group, an undecylene group, a dodecylene group, a phenylene group, a methylphenylene group, a dimethylphenylene group, an ethylphenylene group, a propylphenylene group, a butylphenylene group, a naphthalene group, a toluenediyl group, and a dicyclohexylmethane-4,4'-diyl group. Of those, a hexylene group, a toluenediyl group, or a dicyclohexylmethane-4,4'-diyl group is preferred, and a hexylene group is more preferred. In addition, $R^3$ and $R^4$ each preferably have 6 to 10 carbon atoms. It should be noted that the hydrocarbon group may contain an alkoxyl group such as a methoxy group or an ethoxy group. In addition, those groups are derived from a diisocyanate compound represented by each of the following general formulae (3) and (4), which is used as a raw material when producing the compound represented by general formula (1).

OCN—$R^3$—NCO            (3)

(Where, $R^3$ represents a hydrocarbon group having 4 to 13 carbon atoms.)

OCN—$R^4$—NCO            (4)

(Where, $R^4$ represents a hydrocarbon group having 4 to 13 carbon atoms.)

Examples of such diisocyanate compound include: aliphatic diisocyanates such as tetramethylene diisocyanate, pentamethylene diisocyanate, hexamethylene diisocyanate, 2,2-dimethylpentane diisocyanate, 3-methoxyhexane diisocyanate, octamethylene diisocyanate, 2,2,4-trimethylpentane diisocyanate, nonamethylene diisocyanate, decamethylene diisocyanate, 3-butoxyhexane diisocyanate, dodecamethylene diisocyanate, and 4,4'-biscyclohexylmethane diisocyanate; and aromatic diisocyanates such as meta-phenylene diisocyanate, paraphenylene diisocyanate, 2,4-tolylene diisocyanate, 2,6-tolylene diisocyanate, dimethylbenzene diisocyanate, ethylbenzene diisocyanate, isopropylbenzene diisocyanate, 1,4-naphthalene diisocyanate, 1,5-naphthalene diisocyanate, 2,6-naphthalene diisocyanate, 2,7-naphthalene diisocyanate, and 4,4'-diphenylmethane diisocyanate. Of those, an aliphatic diisocyanate is preferred, an aliphatic diisocyanate compound in which $R^3$ and $R^4$ each have 6 to 10 carbon atoms is more preferred, and hexamethylene diisocyanate is still more preferred. In addition, because the compound represented by general formula (1) can be produced easily, the compound represented by general formula (3) is preferably the same as the compound represented by general formula (4), that is, $R^3$ is preferably the same as $R^4$.

In general formula (1), m and n each are an addition number of moles of an oxyethylene group and each represent a number from 10 to 500, preferably a number from 50 to 150. Further, the values of m and n may be identical to or different from each other and are preferably identical to each other to facilitate production. When the number is less than 10, a gel may not be formed, or the compound represented by general formula (1) may not be produced owing to the viscosity of the product, which is raised excessively during production of the compound. When the number exceeds 500, it takes an excessively long time and an excessively high cost to produce the compound, which is not preferred from an economic standpoint.

In general formula (1), x represents a number from 1 to 1,000, preferably from 50 to 800, more preferably from 100 to 500, still more preferably from 150 to 500, most preferably from 150 to 250. When the x value exceeds 1,000, it takes an excessively long time and an excessively high cost to produce the compound, which is not preferred from an economic standpoint.

In general formula (1), y represents a number from 0 to 10. Although a method of efficiently producing the compound represented by general formula (1) is described in detail below, according to a preferred method, compounds in which y values are different are simultaneously produced. The ratio of the compounds is not particularly specified, and the compound represented by general formula (1) may be produced, for example, as only a compound represented by general formula (1) in which y represents 1 or as a composition comprising certain amounts of compounds each represented by general formula (1) in which y represents a number from 0 to 10. In a composition obtained by mixing the compounds in which y values are different, the mixing ratio of the compounds is not particularly specified, and the ratio of a compound in which y represents a number from 1 to 3 is preferably 50 mass % or more, more preferably 70 mass % or more.

Specific examples of a method of producing the compound represented by general formula (1) include: a method involving adding 1 mol to 1.5 mol each of diisocyanates represented by general formula (3) and general formula (4) to a mixture obtained by adding 0.8 mol to 1.5 mol of polyethylene glycol represented by general formula (7) to 1 mol each of alcohols represented by general formula (5) and general formula (6), and allowing the resultant mixture to react at from 60° C. to 100° C. for from 1 hour to 10 hours; and a method involving adding 1 mol to 1.5 mol each of diisocyanates represented by general formula (3) and general formula (4) to 1 mol of polyethylene glycol represented by general formula (7), allowing the resultant mixture to react at from 60° C. to 100° C. for from 1 hour to 5 hours, adding 0.8 mol to 1.5 mol each of alcohols represented by general formula (5) and general formula (6), and further allowing the resultant mixture to react at the same temperature for from 1 hour to 5 hours. The compounds each represented by general formula (1) and obtained by such methods include 1 mass % to 15 mass % of a compound represented by general formula (1) in which y represents 0, 15 mass % to 50 mass % of a compound represented by general formula (1) in which y represents 1, 10 mass % to 35 mass % of a compound represented by general formula (1) in which y represents 2, and a total of 0 mass % to 74 mass % of compounds each represented by general formula (1) in which y represents 3 or more. In addition, only the compound represented by general formula (1) in which y represents 0 can be produced by adding 1 mol of a diisocyanate represented by general formula (3) to 1 mol each (2 mol in total) of alcohols represented by general formula (5) and general formula (6), and allowing the resultant mixture to react at from 60° C. to 100° C. for from 1 hour to 10 hours.

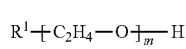
(5)

(Where, $R^1$ represents an alkyl group having 28 to 36 carbon atoms, and m represents a number from 10 to 500.)

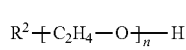
(6)

(Where, $R^2$ represents an alkyl group having 28 to 36 carbon atoms, and n represents a number from 10 to 500.)

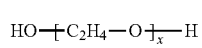
(7)

(Where, x represents a number from 1 to 1,000.)

A catalyst may be used, though the reaction proceeds without a catalyst. For example, the following catalyst may be used as the catalyst at from about 0.01 mass % to 1 mass % with respect to a total of the system: a metal halide such as titanium tetrachloride, hafnium chloride, zirconium chloride, aluminum chloride, gallium chloride, indium chloride, iron chloride, tin chloride, or boron fluoride; a hydroxide, alcoholated product, or carbonate of an alkali metal or alkaline earth metal, such as sodium hydroxide, potassium hydroxide, sodium methylate, or sodium carbonate; a metal oxide such as aluminum oxide, calcium oxide, barium oxide, or sodium oxide; an organic metal compound such as tetraisopropyl titanate, dibutyltin dichloride, dibutyltin oxide, or dibutyltin bis(2-ethylhexyl thioglycolate); or soap such as sodium octylate, potassium octylate, sodium laurate, potassium laurate, sodium acetate, or potassium acetate.

The gel-like composition for a cosmetic preparation of the present invention contains 0.05 part by mass to 3 parts by mass, preferably 0.1 part by mass to 2 parts by mass of the compound represented by general formula (1) with respect to 100 parts by mass of water. When the compound represented by general formula (1) is dissolved completely in water, a clear and colorless gel is obtained. The hardness of the gel can be adjusted by the amount of the compound added. When the amount of the compound added is less than 0.05 part by mass, a gel having adequate hardness cannot be obtained, while when the amount of the compound added exceeds 3 parts by mass, the gel may be hard to use as a gel for a cosmetic preparation because of residual insoluble matters or excessively high hardness of the gel. In addition, the compound represented by general formula (1) may be blended to an emulsion of water and an oil as long as the blending ratio is in the range described above. In this case, a milky-white gel is obtained and can be used for a cosmetic preparation such as a milky lotion or a cream.

To the gel-like composition for a cosmetic preparation of the present invention comprising water and the compound represented by general formula (1) the compound represented by formula (2) may further be added. Preferably, 1 part by weight to 20 parts by weight, more preferably, 2 parts by weight to 10 parts by weight of the compound represented by formula (2) may be added with respect to 100 parts by mass of water in the gel-like composition for a cosmetic preparation of the present invention. The addition of the compound represented by general formula (2) provides an increasing effect on the viscosity of the gel. Therefore, even when the compound represented by general formula (1) is added in a small amount, a gel having desired viscosity can be obtained, leading to economic advantage. In addition, since the gel may contain the compound represented by general formula (1) in a smaller amount, the gel may contain no residues and gives a comfortable feeling of use when applied to the skin. Further, since the gel may contain a relatively larger amount of water, the gel may have relatively higher safety against contact with the skin. If the added amount of the compound represented by general formula (2) is less than 1 part by mass, a thickening effect on a gel may not be achieved. If the added amount of the compound represented by general formula (2) exceeds 20 parts by mass, an effect consistent with the added amount may not be achieved, or the viscosity of the gel may be reduced.

A method of adding the compound represented by general formula (2) is not specified, and may be, for example, a method involving adding the compound represented by general formula (2) to the gel-like composition for a cosmetic preparation of the present invention, which contains water and the compound represented by general formula (1), and mixing the resultant uniformly, or a method involving simultaneously mixing water, the compound represented by general formula (1), and the compound represented by general formula (2).

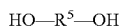
(2)

(Where, $R^5$ represents an alkylene group having 3 to 8 carbon atoms.)

$R^5$ in general formula (2) represents an alkylene group having 3 to 8 carbon atoms. Examples of such alkylene group include a propylene group, an isopropylene group, a butylene group, an isobutylene group, a pentylene group, an isopentylene group, a hexylene group, an isohexylene group, a heptylene group, an octylene group, and an isooctylene group. In addition, specific examples of the compound represented by general formula (2) include 1,2-propanediol (propylene glycol), 1,3-propanediol, 1,2-butanediol, 1,3-butanediol, 1,4-butanediol, 1,2-pentanediol, 1,5-pentanediol, 1,2-hexanediol, 1,6-hexanediol, 1,2-heptanediol, 1,7-heptanediol, 1,2-octanediol, and 1,8-octanediol. Of those, $R^5$ represents preferably an alkylene group having 3 to 6 carbon atoms, more preferably an alkylene group having 3 to 4 carbon atoms, still more preferably an alkylene group having 4 carbon atoms because the compounds each have a high thickening effect on a system.

In addition to the essential components described above, the gel-like composition for a cosmetic preparation of the present invention may appropriately comprise other components used for cosmetic preparations, for example, one or more kinds of powder components, liquid oils and fats, solid oils and fats, wax, hydrocarbons, higher fatty acids, higher alcohols, esters, silicones, anionic surfactants, cationic surfactants, amphoteric surfactants, nonionic surfactants, moisturizing agents, water-soluble polymers, sequestering agents, lower alcohols, polyhydric alcohols, sugars, amino acids, organic amines, polymer emulsions, pH adjustors, skin nutrients, vitamins, and antioxidants, as required within a range in which the effect of the present invention is not impaired. It should be noted that the abbreviation "POE" represents "polyoxyethylene" and the abbreviation "POP" represents "polyoxypropylene" in the following description.

Examples of the powder component include inorganic powders (for example, talc, kaolin, mica, sericite, white mica, bronze mica, synthetic mica, lepidolite, black mica, vermiculite, magnesium carbonate, calcium carbonate, aluminum silicate, barium silicate, calcium silicate, magnesium silicate, strontium silicate, a metal salt of tungstic acid, magnesium, silica, zeolite, barium sulfate, calcined calcium sulfate (calcined gypsum), calcium phosphate, fluorine apatite, hydroxyapatite, ceramic powder, metal soap (for example, zinc myristate, calcium palmitate, or aluminum stearate), and boron nitride); organic powders (for example, polyamide resin powder (nylon powder), polyethylene powder, polymethyl methacrylate powder, polystyrene powder, copolymer resin powder of styrene and acrylic acid, benzoguanamine resin powder, polytetrafluoroethylene powder, and cellulose powder); inorganic white pigments (for example, titanium dioxide and zinc oxide); inorganic red pigments (for example, iron oxide (red iron oxide) and iron titanate); inorganic brown pigments (for example, γ-iron oxide); inorganic yellow pigments (for example, yellow iron oxide and yellow ocher); inorganic black pigments (for example, black iron oxide and lower titanium oxide); inorganic purple pigments (for example, manganese violet and cobalt violet); inorganic green pigments (for example, chromium oxide, chromium hydroxide, and cobalt titanate); inorganic blue pigments (for example, ultramarine blue and Prussian blue); pearl pigments (for example, titanium oxide-coated mica, titanium oxide-coated bismuth oxychloride, titanium oxide-coated talc, colored titanium oxide-coated mica, bismuth oxychloride, and argentine); metal powder pigments (for example, aluminum powder and copper powder); organic pigments such as zirconium, barium, and an aluminum lake (for example, organic pigments such as Red No. 201, Red No. 202, Red No. 204, Red No. 205, Red No. 220, Red No. 226, Red No. 228, Red No. 405, Orange No. 203, Orange No. 204, Yellow No. 205, Yellow No. 401, and Blue No. 404, and Red No. 3, Red No. 104, Red No. 106, Red No. 227, Red No. 230, Red No. 401, Red No. 505, Orange No. 205, Yellow No. 4, Yellow No. 5, Yellow No. 202, Yellow No. 203, Green No. 3, and Blue No. 1); and natural coloring matter (for example, chlorophyl and β-carotene).

Examples of the liquid oils and fats include avocado oil, camellia oil, turtle oil, macadamia nut oil, corn oil, mink oil, olive oil, rapeseed oil, egg-yolk oil, sesame oil, persic oil, wheat germ oil, sasanqua oil, castor oil, linseed oil, safflower oil, cottonseed oil, perilla oil, soybean oil, peanut oil, tea seed oil, kaya oil, rice bran oil, paulownia oil, Japan tung oil, jojoba oil, germ oil, and triglycerin.

Examples of the solid oil and fat include cacao oil, palm oil, hardened palm oil, palm oil, palm kernel oil, Japan wax kernel oil, hardened oil, Japan wax, and hardened castor oil.

Examples of the wax include beeswax, candelilla wax, cotton wax, carnauba wax, bayberry wax, privet wax, whale wax, montan wax, bran wax, lanolin, kapok wax, lanolin acetate, liquid lanolin, sugar cane wax, a lanolin fatty acid isopropyl ester, hexyl laurate, reduced lanolin, jojoba wax, hardened lanolin, shellac wax, POE lanolin alcohol ethers, POE lanolin alcohol acetates, POE cholesterol ethers, lanolin fatty acid polyethylene glycols, and POE hydrogenated lanolin alcohol ethers.

Examples of the hydrocarbon oils include liquid paraffin, ozocerite, squalane, pristane, paraffin, ceresin, squalene, vaseline, and microcrystalline wax.

Examples of the higher fatty acids include lauric acid, myristic acid, palmitic acid, stearic acid, behenic acid, oleic acid, undecylenic acid, a tall oil fatty acid, isostearic acid, linoleic acid, linolenic acid, eicosapentaenoic acid (EPA), and docosahexaenoic acid (DHA).

Examples of the higher alcohol include linear alcohols (for example, lauryl alcohol, cetyl alcohol, stearyl alcohol, behenyl alcohol, myristyl alcohol, oleyl alcohol, and cetostearyl alcohol); and branched alcohols (for example, monostearyl glycerine ether (batyl alcohol), 2-decyltetradecinol, lanolin alcohol, cholesterol, phytosterol, hexyl dodecanol, isostearyl alcohol, and octyl dodecanol).

Examples of the ester oils include isopropyl myristate, cetyl octanoate, octyldodecylmyristate, isopropyl palmitate, butyl stearate, hexyl laurate, myristyl myristate, decyl oleate, hexyldecyl dimethyloctanoate, cetyl lactate, myristyl lactate, lanolin acetate, isocetyl stearate, isocetyl isostearate, cholesteryl 12-hydroxystearate, ethylene glycol di-2-ethylhexylate, a dipentaerythritol fatty acid ester, an N-alkyl glycol monoisostearate, neopentyl glycol dicaprylate, diisostearyl malate, glycerine di-2-heptylundecanoate, trimethylolpropane tri-2-ethylhexylate, trimethyolpropane tri-isostearate, pentaerythritol tetra-2-ethylhexylate, glycerine tri-2-ethylhexylate, glycerin trioctanoate, glycerin triisopalmitate, trimethylolpropane triisostearate, cetyl 2-ethylhexanoate, 2-ethylhexyl palmitate, glycerine trimyristate, tri-2-heptylundecanoic acid glyceride, castor oil fatty acid methyl esters, oleyl oleate, acetoglyceride, 2-heptylundecyl palmitate, diisobutyl adipate, N-lauroyl-L-glutamate-2-octyldodecyl ester, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, and triethyl citrate.

Examples of the silicone oils include chain polysiloxanes (for example, dimethylpolysiloxane, methylphenylpolysiloxane, and diphenylpolysiloxane); ring polysiloxanes (for example, octamethylcyclotetrasiloxane, decamethylcyclopenta siloxane, and dodecamethylcyclohexasiloxane); silicone resins forming a three-dimensional network structure; silicone rubbers; and various modified polysiloxanes (amino-modified polysiloxanes, polyether-modified polysiloxanes, alkyl-modified polysiloxanes, fluorine-modified polysiloxanes, and the like).

Examples of the anionic surfactants include: fatty acid soaps (such as sodium laurate and sodium palmitate); higher alkyl sulfate ester salts (such as sodium lauryl sulfate and potassium lauryl sulfate); alkyl ether sulfate ester salts (such as POE-lauryl sulfate triethanolamine and POE-sodium lauryl sulfate); N-acylsarcosinates (such as sodium lauroylsarcosine); higher fatty acid amide sulfonic acid salts (such as N-myristoyl-N-methyl taurine sodium, a coconut oil fatty acid methyl taurine sodium, and lauryl methyl taurine sodium); phosphoric acid ester salts (POE-sodium oleylether phosphate, POE-stearyl ether phosphoric acid, and the like); sulfosuccinic acid salts (such as sodium di-2-ethylhexyl sulfosuccinate, sodium monolauroyl monoethanolamide polyoxyethylene sulfosuccinate, and sodium lauryl polypropylene glycol sulfosuccinate); alkyl benzenesulfonic acid salts (such as sodium linear dodecylbenzenesulfonate, triethanolamine linear dodecylbenzenesulfonate, and linear dodecylbenzenesulfonic acid); higher fatty acid ester sulfate ester salts (such as a hardened coconut oil fatty acid glycerine sodium sulfate); N-acyl glutamic acid salts (such as monosodium N-lauroyl glutamate, disodium N-stearoyl glutamate, and monosodium N-myristoyl-L-glutamate); sulfonated oils (such as Turkey red oil); POE-alkyl ether carboxylic acids; POE-alkylallyl ether carboxylic acid salts; α-olefinsulfonic acid salts; higher fatty acid ester sulfonic acid salts; secondary alcohol sulfate ester salts; higher fatty acid alkylolamide sulfate ester salts; sodium lauroyl monoethanolamide succinate; N-palmitoyl aspartate ditriethanolamine; and casein sodium.

Examples of the cationic surfactants include: alkyltrimethylammonium salts (such as stearyltrimethylammonium chloride and lauryltrimethylammonium chloride); alkylpyridinium salts (such as cetylpyridinium chloride); distearyldimethylammonium chloride salt; poly(N,N'-dimethyl-3,5-methylenepiperidinium) chloride; alkyl quaternary ammonium salts; alkyldimethylbenzylammonium salts; alkylisoquinolinium salts; dialkylmorpholinium salts; POE-alkylamines; alkylamine salts; polyamine fatty acid derivatives; amyl alcohol fatty acid derivatives; benzalkonium chloride; and benzethonium chloride.

Examples of the amphoteric surfactant include: imidazoline-based amphoteric surfactants (such as sodium 2-undecyl-N,N,N-(hydroxyethylcarboxymethyl)-2-imidazoline, and 2-cocoyl-2-imidazolium hydroxide-1-carboxyethyloxy disodium salt); and betaine-based surfactants (such as 2-heptadecyl-N-carboxymethyl-N-hydroxyethylimidazolium betaine, betaine lauryldimethylaminoacetate, alkylbetaines, amidobetaines, and sulfobetaines).

Examples of the nonionic surfactant include: sorbitan fatty acid esters (such as sorbitan monooleate, sorbitan monoisostearate, sorbitan monolaurate, sorbitan monopalmitate, sorbitan monostearate, sorbitan sesquioleate, sorbitan trioleate, diglycerolsorbitanpenta-2-ethylhexylate, and diglycerol sorbitan tetra-2-ethylhexylate); glycerin polyglycerin fatty acids (such as a monocottonseed oil fatty acid glycerin, glycerin monoerucate, glycerin sesquioleate, glycerin monostearate, glycerin α,α'-oleate pyroglutamate, and glycerin monostearate malate); propylene glycol fatty acid esters (such as propylene glycol monostearate); hydrogenated castor oil derivatives; a glycerin alkyl ether; POE-sorbitan fatty acid esters (such as POE-sorbitan monooleate, POE-sorbitan monostearate, POE-sorbitan monooleate, and POE-sorbitan tetraoleate); POE-sorbit fatty acid esters (such as POE-sorbit monolaurate, POE-sorbit monooleate, POE-sorbit pentaoleate, and POE-sorbit monostearate); POE-glycerin fatty acid esters (such as POE-monooleates, e.g., POE-glycerin monostearate, POE-glycerin monoisostearate, and POE-glycerin triisostearate); POE-fatty acid esters (such as POE-distearate, POE-monodioleate, and ethylene glycol distearate); POE-alkyl ethers (such as POE-lauryl ether, POE-oleyl ether, POE-stearyl ether, POE-behenyl ether, POE-2-octyldodecyl ether, and POE-cholestanol ether); Pluronic-type surfactants (such as Pluronic); POE/POP-alkyl ethers (such as POE/POP-cetyl ether, POE/POP-2-decyltetradecyl ether, POE/POP-monobutyl ether, POE/POP-hydrogenated lanolin, and POE/POP-glycerin ether); tetra POE/tetra POP-ethylenediamine condensates (such as Tetronic); POE-castor oil/hydrogenated castor oil derivatives (such as POE-castor oil, POE-hydrogenated castor oil, POE-hydrogenated castor oil monoisostearate, POE-hydrogenated castor oil triisostearate, POE-hydrogenated castor oil monopyroglutamic acid monoisostearic acid diester, and POE-hydrogenated castor oil maleic acid ester); a POE-beeswax/lanolin derivative (such as POE-sorbit beeswax); alkanolamides (such as coconut oil fatty acid diethanolamides, lauric acid monoethanol amide, and a fatty acid isopropanolamide); POE-propylene glycol fatty acid esters; POE-alkylamines; POE-fatty acid amides; sucrose fatty acid esters; alkylethoxydimethylamine oxides; and trioleyl phosphate.

Examples of the moisturizing agent include polyethylene glycol, xylitol, sorbitol, maltitol, chondroitin sulfate, hyaluronic acid, mucoitinsulfuric acid, charonic acid, atelocollagen, cholesteryl-12-hydroxystearate, sodium lactate, bile acid salts, dl-pyrrolidonecarboxylic acid salts, short-chain soluble collagens, diglycerin (EO)PO adducts, rosa roxburghii extracts, yarrow extracts, and sweet clover extracts.

As a natural water-soluble polymer, there are given, for example: vegetable-based polymers (such as gum arabic, gum tragacanth, galactan, guar gum, carob gum, gum karaya, carrageenan, pectin, agar, a quince seed (quince), algae colloid (brown alga extract), starch (rice, corn, potato, and wheat), and glycyrrhizic acid); microorganism-based polymers (such as xanthane gum, dextran, succinoglucan, pullulan, and gellan gum); and animal-based polymers (such as collagen, casein, albumin, and gelatin).

Examples of the water-soluble polymer include: starch-based polymers (such as carboxymethyl starch and methylhydroxypropyl starch); cellulose-based polymers (such as methylcellulose, ethylcellulose, methylhydroxypropylcellulose, hydroxyethylcellulose, sodium cellulose sulfate, hydroxypropylcellulose, carboxymethylcellulose, sodium carboxymethylcellulose, crystalline cellulose, and cellulose powder); alginic acid-based polymers (such as sodium alginate and propylene glycol alginate ester); vinyl-based polymers (such as polyvinyl alcohol, polyvinyl methyl ether, polyvinylpyrrolidone, and a carboxyvinyl polymer); polyoxyethylene-based polymers (such as polyoxyethylene-polyoxypropylene copolymers of polyethylene glycol 20,000, 40,000, or 60,000); acrylic polymers (such as sodium polyacrylate, polyethyl acrylate, and polyacrylamide); polyethylene imine; and cationic polymers.

Examples of the sequestering agent include 1-hydroxyethane-1,1-diphosphonic acid, 1-hydroxyethane-1,1-diphosphonic acid tetrasodium salts, disodium edetate, trisodium edetate, tetrasodium edetate, sodium citrate, sodium polyphosphate, sodium metaphosphate, gluconic acid, phosphoric acid, citric acid, ascorbic acid, succinic acid, edetic acid, and trisodium ethylenediamine hydroxyethyl triacetate.

Examples of the lower alcohol include ethanol, propanol, isopropanol, isobutyl alcohol, and t-butyl alcohol.

Examples of the polyhydric alcohol include: trihydric alcohols (such as glycerine and trimethylolpropane); tetrahydric alcohols (such as pentaerythritol of 1,2,6-hexanetriol or the like); pentahydric alcohols (such as xylitol); hexahydric alcohols (such as sorbitol and mannitol); polyhydric alcohol polymers (such as diethylene glycol, dipropylene glycol, triethylene glycol, polypropylene glycol, tetraethylene glycol, diglycerine, polyethylene glycol, triglycerine, tetraglycerine, and polyglycerine); dihydric alcohol alkyl ethers (such as ethylene glycol monomethyl ether, ethylene glycol monoethyl ether, ethylene glycol monobutyl ether, ethylene glycol monophenyl ether, ethylene glycol monohexyl ether, ethylene glycol mono-2-methylhexyl ether, ethylene glycol isoamyl ether, ethylene glycol benzyl ether, ethylene glycol isopropyl ether, ethylene glycol dimethyl ether, ethylene glycol diethyl ether, and ethylene glycol dibutyl ether); dihydric alcohol alkyl ethers (such as diethylene glycol monomethyl ether, diethylene glycol monoethyl ether, diethylene glycol monobutyl ether, diethylene glycol dimethyl ether, diethylene glycol diethyl ether, diethylene glycol butyl ether, diethylene glycol methyl ethyl ether, triethylene glycolmonomethyl ether, triethylene glycol monoethyl ether, propylene glycol monomethyl ether, propylene glycol monoethyl ether, propylene glycol monobutyl ether, propylene glycol isopropyl ether, dipropylene glycol methyl ether, dipropylene glycol ethyl ether, and dipropylene glycol butyl ether); dihydric alcohol ether esters (such as ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disuccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate, and propylene glycol monophenyl ether acetate); glycerine monoalkyl ethers (such as chimyl alcohol, serachyl alcohol, and batyl alcohol); sugar alcohols (such as sorbitol, maltitol, maltotriose, mannitol, sucrose, erythritol, glucose, fructose, amylolysis sugars, maltose, xylitose, and alcohols prepared by reduction of amylolysis sugars); Glysolid; tetrahydrofurfuryl alcohol; POE-tetrahydrofurfuryl alcohol; POP-butyl ether; POP/POE-butyl ether; tripolyoxypropylene glycerin ether; POP-glycerine ether; POP-glycerine ether phosphoric acid; POP/POE-pentaneerythritol ether; and polyglycerin.

As a monosaccharide, there are given, for example: trioses (such as D-glyceryl aldehyde and dihydroxy acetone); tetroses (such as D-erythrose, D-erythrulose, D-threose, and erythritol); pentoses (such as L-arabinose, D-xylose, L-lixose, D-arabinose, D-ribose, D-ribulose, D-xylulose, and L-xylulose); hexoses (such as D-glucose, D-talose, D-psicose, D-galactose, D-fructose, L-galactose, L-mannose, and D-tagatose); heptoses (such as aldoheptose and heptulose); octoses (such as octulose); deoxy sugars (such as 2-deoxy-D-ribose, 6-deoxy-L-galactose, and 6-deoxy-L-mannose); amino acids (such as D-glucosamine, D-galactosamine, sialic acid, amino uronic acid, and muramic acid); and uronic acids (such as D-glucuronic acid, D-mannuronic acid, L-guluronic acid, D-galacturonic acid, and L-iduronic acid).

As an oligosaccharide, there are given, for example, sucrose, umbelliferose, lactose, planteose, isolychnoses, α,α-trehalose, raffinose, lychnoses, umbilicin, and stachyose-verbascoses.

As a polysaccharide, there are given, for example, cellulose, quince seed, chondroitin sulfate, starch, galactan, dermatan sulfate, glycogen, gum arabic, heparan sulfate, hyaluronic acid, gum tragacanth, keratan sulfate, chondroitin, xanthane gum, mucoitinsulfuric acid, guar gum, dextran, keratosulfate, locust bean gum, succinoglucan, and charonic acid.

Examples of the amino acid include: neutral amino acids (such as threonine and cysteine); and basic amino acids (such as hydroxylysine). In addition, as amino acid derivatives, there are given, for example, acylsarcosine sodium (lauroylsarcosine sodium), acylglutamic acid salts, acyl β-alanine sodium, glutathione, and pyrrolidone carboxylic acid.

Examples of the organic amines include monoethanolamine, diethanol amine, triethanol amine, morpholine, triisopropanolamine, 2-amino-2-methyl-1,3-propanediol, and 2-amino-2-methyl-1-propanol.

Examples of the polymer emulsion include acrylic resin emulsions, polyethyl acrylate emulsions, acrylic resin liquid, polyacrylic alkyl ester emulsions, polyvinyl acetate resin emulsions, and natural rubber latexes.

Examples of the pH adjustor include buffers such as lactic acid-sodium lactate, citric acid-sodium citrate, and succinic acid-sodium succinate.

Examples of the vitamin include vitamins A, B1, B2, B6, C, and E, and derivatives thereof, pantothenic acid and a derivative thereof, and biotin.

Examples of the antioxidant include tocopherols, dibutylhydroxy toluene, butylhydroxy anisole, and gallic acid esters.

Examples of other components that can be added include: preservatives (such as methylparaben, ethylparaben, butylparaben, and phenoxyethanol); antiphlogistic agents (such as glycyrrhizic acid derivatives, glycyrrhetinic acid derivatives, salicylic acid derivatives, hinokitiol, zinc oxide, and allantoin); whitening agents (such as saxifrage extracts and arbutin); various extracts (extracts of Phellodendron bark, *Coptis japonica*, lithospermum root, *Paeonia lactiflora*, *Swertia japonica*, birch, sage, loquat, carrot, aloe, mallow, iris, grapevine, coix seed, dishcloth gourd, lily, saffron, Cnidium rhizome, ginger, hypericum, *Ononis spinosa*, a garlic, capsicum, Citrus Unshiu Peel, *Angelica acutiloba*, seaweed, or the like); activators (such as royal jelly, a photosensitive element, and cholesterol derivatives); circulation promoters (such as benzyl nicotinate ester, β-butoxyethyl nicotinate ester, capsaicin, zingerone, Cantharides tincture, ichthammol, tannic acid, α-borneol, tocopherol nicotinate, inositol hexanicotinate, cyclandelate, cinnarizine, tolazoline, acetylcholine, verapamil, cepharanthine, and γ-orizanol); antiseborrheic agents (such as sulfur and thianthol); and anti-inflammatory agents (such as tranexamic acid, thiotaurine, and hypotaurine).

The cosmetic preparation of the present invention is a cosmetic preparation containing the gel-like composition for a cosmetic preparation of the present invention. The gel-like composition for a cosmetic preparation of the present invention can be prepared as a viscous liquid having fluidity or as an elastic gel by adjusting the added amount of the compound represented by general formula (1) or the like. The form of the gel may be appropriately selected depending on the type of cosmetic preparation for which the gel-like composition is used. It should be noted that the amount of the compound represented by general formula (1), which is added to the cosmetic preparation, varies depending on the type of cosmetic preparation, and the gel-like composition for a cosmetic preparation of the present invention is used so that the cosmetic preparation of the present invention usually contains 0.03 mass % to 2.5 mass %, preferably 0.05 mass % to 2.0 mass % of the compound represented by general formula (1).

Examples of the cosmetic preparation for which the gel-like composition can be used include a cream, face-washing creams, face-washing foams, cleansing creams, cleansing milks, cleansing lotions, massage creams, moisture creams, suntan creams, hair liquids, set lotions, hair bleaches, color rinses, permanent wave solutions, hand creams, lipsticks, liquid foundations, cosmetic washes, cosmetic solutions, milky lotions, Eau de Cologne, nail cosmetics, mascara, eyeliner, shampoos, rinses, treatments, and a body soaps. Of those, the gel-like composition is preferably used for creams, beauty solutions, cosmetic washes, milky lotions, liquid foundations, or the like, which are directly applied to the skin, because of a favorable feeling of use when applied to the skin.

Examples

Hereinafter, the present invention is described specifically by way of examples. The present invention is not limited by the examples, and may vary without departing from the scope of the present invention. It should be noted that the term "EO" as used in the following description refers to "ethylene oxide."

<Production of Samples>

800 g (0.1 mol) of polyoxyethylene glycol having a weight-average molecular weight of 8,000 (PEG 1) and 522 g (0.2 mol) of an adduct of an alcohol having 28 carbon atoms (2-dodecylhexadecanol) with 50 mol of EO (alcohol 1) were added to a 3,000-ml volume four-necked flask with a thermometer, a nitrogen introducing pipe, and an agitator, and dissolved by mixing at from 80° C. to 90° C. Subsequently, 34 g (0.2 mol) of hexamethylene diisocyanate (HDI) was added to the system, and the mixture was allowed to react at from 80° C. to 90° C. for 3 hours to afford compound 1. It should be noted that compounds 2 to 17 were produced using the following raw materials in the same apparatus by the same method. Reaction ratios of the raw materials of the compounds are shown in Tables 1 and 2.

<Raw Materials Used in Production of Samples>

Alcohol 1: An adduct of 2-dodecylhexadecanol (having 28 carbon atoms) with 50 mol of EO
Alcohol 2: An adduct of 2-tetradecylhexadecanol (having 30 carbon atoms) with 50 mol of EO
Alcohol 3: An adduct of 2-tetradecyloctadecanol (having 32 carbon atoms) with 50 mol of EO
Alcohol 4: An adduct of 2-hexadecyloctadecanol (having 34 carbon atoms) with 50 mol of EO
Alcohol 5: An adduct of 2-hexadecyleicosanol (having 36 carbon atoms) with 50 mol of EO
Alcohol 6: An adduct of 2-tetradecyloctadecanol (having 32 carbon atoms) with 100 mol of EO
Alcohol 7: An adduct of 2-tetradecyloctadecanol (having 32 carbon atoms) with 200 mol of EO
Alcohol 8: An adduct of 2-dodecyltetradecanol (having 26 carbon atoms) with 50 mol of EO
Alcohol 9: An adduct of 2-decyltetradecanol (having 24 carbon atoms) with 50 mol of EO
Alcohol 10: An adduct of stearyl alcohol (having 18 carbon atoms) with 50 mol of EO
PEG 1: Polyethylene glycol (having a weight-average molecular weight of 8,000)
PEG 2: Polyethylene glycol (having a weight-average molecular weight of 10,000)
PEG 3: Polyethylene glycol (having a weight-average molecular weight of 20,000)
HDI: Hexamethylene diisocyanate
H-MDI: 4,4'-Biscyclohexylmethane diisocyanate
TDI: Tolylene diisocyanate
PG: Propylene glycol
BD: 1,3-Butanediol
HD: 1,2-Hexanediol
OD: 1,2-Octanediol
EG: Ethylene glycol
DD: 1,2-Decanediol
BA: Butanol
GL: Glycerin

TABLE 1

Reaction ratios of produced samples

| | Compounds | | | | | | | | | | |
|---|---|---|---|---|---|---|---|---|---|---|---|
| | 1 | 2 | 3 | 4 | 5 | 6 | 7 | 8 | 9 | 10 | 11 |
| Alcohol 1 | 2 | | | | | | | | | | |
| Alcohol 2 | | 2 | | | | | | | | | |
| Alcohol 3 | | | 2 | | | | | 2 | 2 | 2 | 2 |
| Alcohol 4 | | | | 2 | | | | | | | |
| Alcohol 5 | | | | | 2 | | | | | | |
| Alcohol 6 | | | | | | 2 | | | | | |
| Alcohol 7 | | | | | | | 2 | | | | |
| PEG 1 | 1 | 1 | 1 | 1 | 1 | 1 | 1 | | | 1 | 1 |
| PEG 2 | | | | | | | | 1 | | | |
| PEG 3 | | | | | | | | | 1 | | |
| HDI | 2 | 2 | 2 | 2 | 2 | 2 | 2 | 2 | 2 | | |
| H-MDI | | | | | | | | | | 2 | |
| TDI | | | | | | | | | | | 2 |

*Numbers in the table represent molar ratios of each raw material.

TABLE 2

Reaction ratios of produced samples

| | Compounds | | | | | |
|---|---|---|---|---|---|---|
| | 12 | 13 | 14 | 15 | 16 | 17 |
| Alcohol 8 | 2 | | | 2 | 2 | 2 |
| Alcohol 9 | | 2 | | | | |
| Alcohol 10 | | | 2 | | | |
| PEG 1 | 1 | 1 | 1 | | 1 | |
| PEG 2 | | | | | | 1 |
| PEG 3 | | | | 1 | | |
| HDI | 2 | 2 | 2 | 2 | | |
| H-MDI | | | | | 2 | |
| TDI | | | | | | 2 |

*Numbers in the table represent molar ratios of each raw material.

Compound 1: m=n=50, $R^1=R^2$=2-dodecylhexadecyl group, $R^3=R^4$=hexylene group
Compound 2: m=n=50, $R^1=R^2$=2-tetradecylhexadecyl group, $R^3=R^4$=hexylene group
Compound 3: m=n=50, $R^1=R^2$=2-tetradecyloctadecyl group, $R^3=R^4$=hexylene group
Compound 4: m=n=50, $R^1=R^2$=2-hexadecyloctadecyl group, $R^3=R^4$=hexylene group
Compound 5: m=n=50, $R^1=R^2$=2-hexadecyleicosyl group, $R^3=R^4$=hexylene group
Compound 6: m=n=100, 2 tetradecyloctadecyl group, $R^3=R^4$=hexylene group
Compound 7: m=n=200, $R^1=R^2$=2-tetradecyloctadecyl group, $R^3=R^4$=hexylene group
Compound 8: m=n=50, $R^1=R^2$=2-tetradecyloctadecyl group, $R^3=R^4$=hexylene group
Compound 9: m=n=50, $R^1=R^2$=2-tetradecyloctadecyl group, $R^3=R^4$=hexylene group
Compound 10: m=n=50, $R^1=R^2$=2-tetradecyloctadecyl group, $R^3=R^4$=dicyclohexylmethane-4,4'-diyl group
Compound 11: m=n=50, $R^1=R^2$=2-tetradecyloctadecyl group, $R^3=R^4$=toluenediyl group
Compound 12: m=n=50, $R^1=R^2$=2-dodecyltetradecyl group, $R^3=R^4$=hexylene group
Compound 13: m=n=50, $R^1=R^2$=2-decyltetradecyl group, $R^3=R^4$=hexylene group
Compound 14: m=n=50, $R^1=R^2$=octadecyl group, $R^3=R^4=(CH_2)_6$
Compound 15: m=n=50, $R^1=R^2$=2-dodecyltetradecyl group, $R^3=R^4$=hexylene group Compound 16: m=n=50, $R^1$=$R^2$=2-dodecyltetradecyl group, $R^3$=$R^4$=dicyclohexylmethane-4,4'-diyl group Compound 17: m=n=100, $R^1$=$R^2$=2-dodecyltetradecyl group, $R^3$=$R^4$=toluenediyl group It should be noted that y values in the compounds 1 to 17 were determined by the following method.

<Analysis by GPC>

Molecular weight distributions of the compounds obtained in "Production of Samples" were measured by gel permeation chromatography (GPC), and the y values were calculated based on area ratios of the resultant charts. It should be noted that the device and conditions used for the measurement are described below.

Used columns: TSK gel G4000HX1, G3000HX1, G2000HX1 (all of which are manufactured by Tosoh Corporation) were connected in series.

Eluent: Tetrahydrofuran (THF)
Flow rate: 1 ml/min
Detector: HLC-8120GPC (RI)
Sample concentration: 0.1 mass % (THF solution)
Sample amount: 200 μl
Column temperature: 40° C.

The y values calculated by the method are shown below. In addition, x values in the compounds 1 to 17 are shown in the following table.

TABLE 3

| Compound | x | y = 0 | y = 1 | y = 2 | 10 ≥ y ≥ 3 |
|---|---|---|---|---|---|
| 1 | 181 | 2 | 32 | 20 | 46 |
| 2 | 181 | 2 | 31 | 21 | 46 |
| 3 | 181 | 2 | 30 | 22 | 46 |
| 4 | 181 | 2 | 31 | 19 | 48 |
| 5 | 181 | 2 | 34 | 21 | 43 |
| 6 | 181 | 2 | 33 | 20 | 45 |

TABLE 3-continued

| Compound | x | y = 0 | y = 1 | y = 2 | 10 ≥ y ≥ 3 |
|---|---|---|---|---|---|
| 7 | 181 | 2 | 32 | 21 | 45 |
| 8 | 227 | 3 | 28 | 17 | 52 |
| 9 | 454 | 1 | 36 | 24 | 39 |
| 10 | 181 | 2 | 32 | 21 | 45 |
| 11 | 181 | 2 | 33 | 19 | 46 |
| 12 | 181 | 2 | 33 | 21 | 44 |
| 13 | 181 | 2 | 31 | 23 | 44 |
| 14 | 181 | 2 | 30 | 32 | 46 |
| 15 | 454 | 1 | 37 | 25 | 37 |
| 16 | 181 | 2 | 31 | 20 | 47 |
| 17 | 227 | 2 | 32 | 21 | 45 |

Unit of each y value: mass %

(Evaluation of Products of the Present Invention and Comparative Products)

In conformity with the formulations shown in Tables 4 and 5, the compounds 1 to 17 were added to water and uniformly dissolved by mixing, to thereby prepare gels. In addition, the compounds 1 to 17, water, and various alcohols were mixed to prepare gels. The viscosities of the gels prepared were measured, and the gels were each evaluated by ten panelists according to the following method for use feeling (moist feeling, lack of sticky feeling, compatibility, or residue-free feeling) when applied to the skin. The results are shown in Tables 4 and 5. Further, the viscosities at 25° C. of the gels were measured with a B-type viscometer.

(Evaluation)

∘∘: Eight or more panelists answered that the sample gave a good feeling of use.

∘: Six or seven panelists answered that the sample gave a good feeling of use.

Δ: Three to five panelists answered that the sample gave a good feeling of use.

x: Two or less panelists answered that the sample gave a good feeling of use.

TABLE 4

| | | Example | | | | | | | | | | |
|---|---|---|---|---|---|---|---|---|---|---|---|---|
| | | 1 | 2 | 3 | 4 | 5 | 6 | 7 | 8 | 9 | 10 | 11 |
| Compound | 1 | 1 | | | | | | | | | | |
| | 2 | | 1 | | | | | | | | | |
| | 3 | | | 1 | | | | | | | | |
| | 4 | | | | 1 | | | | | | | |
| | 5 | | | | | 1 | | | | | | |
| | 6 | | | | | | 1 | | | | | |
| | 7 | | | | | | | 1 | | | | |
| | 8 | | | | | | | | 1 | | | |
| | 9 | | | | | | | | | 1 | | |
| | 10 | | | | | | | | | | 1 | |
| | 11 | | | | | | | | | | | 1 |
| | 12 | | | | | | | | | | | |
| | 13 | | | | | | | | | | | |
| | 14 | | | | | | | | | | | |
| | 15 | | | | | | | | | | | |
| | 16 | | | | | | | | | | | |
| | 17 | | | | | | | | | | | |
| PG | | | | | | | | | | | | |
| BD | | | | | | | | | | | | |
| HD | | | | | | | | | | | | |
| OD | | | | | | | | | | | | |
| EG | | | | | | | | | | | | |
| DD | | | | | | | | | | | | |
| BA | | | | | | | | | | | | |
| GL | | | | | | | | | | | | |
| Water | | 100 | 100 | 100 | 100 | 100 | 100 | 100 | 100 | 100 | 100 | 100 |
| Viscosity (mPa · s) | | 4,700 | 4,600 | 4,600 | 4,500 | 4,500 | 4,700 | 4,800 | 4,600 | 4,700 | 4,800 | 4,200 |

TABLE 4-continued

|  | Example | | | | | | | | | | |
|---|---|---|---|---|---|---|---|---|---|---|---|
|  | 1 | 2 | 3 | 4 | 5 | 6 | 7 | 8 | 9 | 10 | 11 |
| Moist feeling | ○ | ○ | ○○ | ○ | ○ | ○○ | ○○ | ○○ | ○○ | ○○ | ○○ |
| Lack of sticky feeling | ○○ | ○○ | ○○ | ○○ | ○○ | ○○ | ○○ | ○○ | ○○ | ○○ | ○○ |
| Compatibility | ○ | ○○ | ○○ | ○○ | ○○ | ○○ | ○ | ○○ | ○○ | ○○ | ○ |
| Residue-free feeling | ○○ | ○○ | ○○ | ○○ | ○○ | ○○ | ○○ | ○○ | ○○ | ○○ | ○○ |

TABLE 5

|  |  | Example | | | | | | | | | | |
|---|---|---|---|---|---|---|---|---|---|---|---|---|
|  |  | 12 | 13 | 14 | 15 | 16 | 17 | 18 | 19 | 20 | 21 | 22 |
| Compound | 1 | | | | | | | | | | | |
|  | 2 | | | | | | | | | | | |
|  | 3 | 0.5 | 0.5 | 0.5 | 0.5 | 0.5 | 0.5 | 0.5 | 0.5 | 0.5 | 0.5 | 0.5 |
|  | 4 | | | | | | | | | | | |
|  | 5 | | | | | | | | | | | |
|  | 6 | | | | | | | | | | | |
|  | 7 | | | | | | | | | | | |
|  | 8 | | | | | | | | | | | |
|  | 9 | | | | | | | | | | | |
|  | 10 | | | | | | | | | | | |
|  | 11 | | | | | | | | | | | |
|  | 12 | | | | | | | | | | | |
|  | 13 | | | | | | | | | | | |
|  | 14 | | | | | | | | | | | |
|  | 15 | | | | | | | | | | | |
|  | 16 | | | | | | | | | | | |
|  | 17 | | | | | | | | | | | |
| PG |  | | 3 | | | | | | | | | |
| BD |  | | | 3 | | | | | | | 5 | 10 |
| HD |  | | | | 3 | | | | | | | |
| OD |  | | | | | 3 | | | | | | |
| EG |  | | | | | | 3 | | | | | |
| DD |  | | | | | | | 3 | | | | |
| BA |  | | | | | | | | 3 | | | |
| GL |  | | | | | | | | | 3 | | |
| Water | | 100 | 100 | 100 | 100 | 100 | 100 | 100 | 100 | 100 | 100 | 100 |
| Viscosity (mPa · s) | | 2,200 | 4,200 | 4,800 | 4,300 | 2,100 | 2,200 | 2,100 | 2,100 | 2,200 | 16,300 | 53,200 |
| Moist feeling | | ○○ | ○○ | ○○ | ○○ | ○○ | ○○ | ○○ | ○○ | ○○ | ○○ | ○ |
| Lack pf sticky feeling | | ○○ | ○○ | ○○ | ○○ | ○○ | ○○ | ○○ | ○○ | ○○ | ○○ | ○○ |
| Compatibility | | ○○ | ○○ | ○○ | ○○ | ○○ | ○○ | ○○ | ○○ | ○○ | ○○ | ○○ |
| Residue-free feeling | | ○○ | ○○ | ○○ | ○○ | ○○ | ○○ | ○○ | ○○ | ○○ | ○○ | ○○ |

TABLE 6

|  |  | Comparative Example | | | | | | | | | |
|---|---|---|---|---|---|---|---|---|---|---|---|
|  |  | 1 | 2 | 3 | 4 | 5 | 6 | 7 | 8 | 9 | 10 |
| Compound | 1 | | | | | | | | | | |
|  | 2 | | | | | | | | | | |
|  | 3 | | | | | | | | | | |
|  | 4 | | | | | | | | | | |
|  | 5 | | | | | | | | | | |
|  | 6 | | | | | | | | | | |
|  | 7 | | | | | | | | | | |
|  | 8 | | | | | | | | | | |
|  | 9 | | | | | | | | | | |
|  | 10 | | | | | | | | | | |
|  | 11 | | | | | | | | | | |
|  | 12 | 1 | | | | | | 1 | | 1 | |
|  | 13 | | 1 | | | | | | 1 | | |
|  | 14 | | | 1 | | | | | | 1 | |

TABLE 6-continued

| | Comparative Example | | | | | | | | | |
|---|---|---|---|---|---|---|---|---|---|---|
| | 1 | 2 | 3 | 4 | 5 | 6 | 7 | 8 | 9 | 10 |
| 15 | | | | 1 | | | | | | |
| 16 | | | | | 1 | | | | | |
| 17 | | | | | | 1 | | | | |
| PG | | | | | | | 3 | | | |
| BD | | | | | | | | 3 | | |
| HD | | | | | | | | | 3 | |
| OD | | | | | | | | | | 1 |
| EG | | | | | | | | | | 2 |
| DD | | | | | | | | | | |
| BA | | | | | | | | | | |
| GL | | | | | | | | | | |
| Water | 100 | 100 | 100 | 100 | 100 | 100 | 100 | 100 | 100 | 100 |
| Viscosity (mPa · s) | 4,500 | 4,500 | 650 | 4,700 | 4,600 | 4,700 | 9,200 | 10,500 | 800 | 9,000 |
| Moist feeling | x | x | x | x | x | x | x | x | x | x |
| Lack of sticky feeling | ○ | ○ | ○ | ○ | ○ | ○ | ○ | ○ | ○ | ○ |
| Compatibility | ○ | ○ | Δ | ○ | ○ | ○ | ○ | ○ | Δ | ○ |
| Residue-free feeling | ○○ | ○○ | ○○ | ○○ | ○○ | ○○ | ○○ | ○○ | ○○ | ○○ |

Three kinds of gelling agents, i.e., compound 1, xanthane gum (manufactured by Tokyo Chemical Industry Co., Ltd.), and a carboxyvinyl polymer (Carbopol 980, manufactured by Lubrizol Japan Limited) were dissolved in water to prepare gel-like substances. Specifically, a gel comprising a 2 mass % aqueous solution of compound 1, a gel comprising a 3 mass % aqueous solution of the xanthane gum, and a gel comprising a 1 mass % aqueous solution of the carboxyvinyl polymer were prepared, and each of the gels was adjusted to pH 9 with triethanolamine.

Behaviors of each of the gels were measured continuously with a rheometer (shear rate range: $0.01\ s^{-1}$ to $0.4\ s^{-1}$) after addition of a salt (NaCl) to each of the gel-like substances at 3 mass % with respect to the total amount of the gel and after addition of hydrochloric acid to the gel-like substance to change the pH to 1.7. The device used and measurement conditions are as described below.

<Used Instrument>

Name of apparatus: MCR301 (manufactured by Anton Paar GmbH)

<Measurement Condition>

Measurement jig: CP25-2 (cone plate, φ25 mm, angle: 2°)

Measurement position: 0.104 mm (distance from stage to parallel plate)

Measurement temperature: 25° C.

(1) When Salt was Added

TABLE 7

| | Compound 1 | | |
|---|---|---|---|
| | Viscosity (mPa · s) | | |
| | Shear rate $0.01\ s^{-1}$ | Shear rate $0.1\ s^{-1}$ | Shear rate $0.3\ s^{-1}$ |
| Addition amount of salt: 0 mass % | $1.51 \times 10^5$ | $1.49 \times 10^5$ | $1.52 \times 10^5$ |
| Addition amount of salt: 3 mass % | $1.54 \times 10^5$ | $1.56 \times 10^5$ | $1.71 \times 10^5$ |

TABLE 8

| | Xanthane gum | | |
|---|---|---|---|
| | Viscosity (mPa · s) | | |
| | Shear rate $0.01\ s^{-1}$ | Shear rate $0.1\ s^{-1}$ | Shear rate $0.4\ s^{-1}$ |
| Addition amount of salt: 0 mass % | $9.5 \times 10^5$ | $7.0 \times 10^4$ | $4.0 \times 10^4$ |
| Addition amount of salt: 3 mass % | $1.2 \times 10^6$ | $4.3 \times 10^5$ | $1.0 \times 10^5$ |

TABLE 9

| | Carboxyvinyl polymer | | |
|---|---|---|---|
| | Viscosity (mPa · s) | | |
| | Shear rate $0.01\ s^{-1}$ | Shear rate $0.1\ s^{-1}$ | Shear rate $0.4\ s^{-1}$ |
| Addition amount of salt: 0 mass % | $2.4 \times 10^9$ | $4.3 \times 10^8$ | $2.4 \times 10^8$ |
| Addition amount of salt: 3 mass % | $4.1 \times 10^4$ | $9.6 \times 10^2$ | $7.7 \times 10^1$ |

(2) When pH was Changed

The values of viscosities when the pH was changed from 9 to 1.7 were compared at a shear rate of $0.01\ s^{-1}$.

TABLE 10

| | pH 9 | pH 1.7 |
|---|---|---|
| Compound 1 | $1.51 \times 10^5$ | $1.01 \times 10^5$ |
| Xanthane gum | $9.1 \times 10^5$ | $6.3 \times 10^5$ |
| Carboxyvinyl polymer | $1.51 \times 10^5$ | unmeasurable |

*It should be noted that the gel prepared from the carboxyvinyl polymer was completely destroyed by lowering its pH, and its viscosity could not be measured.

The viscosity of the carboxyvinyl polymer was significantly changed both by the addition of the salt and by the change in pH. Although the viscosity of the xanthane gum was changed similarly to compound 1 by the change in pH, it was significantly changed by the addition of the salt as compared to compound 1. Compound 1 had less change in viscosity and was stable in both cases.

The invention claimed is:

1. A gel-like composition for a cosmetic preparation, comprising 0.05 part by mass to 3 parts by mass of a compound represented by the following formula (1) with respect to 100 parts by mass of water:

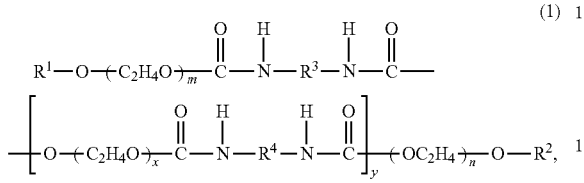

wherein $R^1$ and $R^2$ each represent an alkyl group having 28 to 36 carbon atoms, $R^3$ and $R^4$ each represent a hydrocarbon group having 4 to 13 carbon atoms, m and n each represent a number from 10 to 500, x represents a number from 1 to 1,000, and y represents a number from 0 to 10.

2. The gel-like composition for a cosmetic preparation according to claim 1, wherein $R^1$ and $R^2$ in formula (1) each represent an alkyl group having 32 carbon atoms.

3. The gel-like composition for a cosmetic preparation according to claim 2, wherein $R^1$ and $R^2$ each represent a 2-tetradecyloctadecyl group.

4. The gel-like composition for a cosmetic preparation according to claim 1, further comprising 1 part by mass to 20 parts by mass of a compound represented by the following formula (2) with respect to 100 parts by mass of water:

where wherein $R^5$ represents an alkylene group having 3 to 8 carbon atoms.

5. A cosmetic preparation, comprising the gel-like composition for a cosmetic preparation according to claim 1.

6. The gel-like composition for a cosmetic preparation according to claim 2, further comprising 1 part by mass to 20 parts by mass of a compound represented by the following formula (2) with respect to 100 parts by mass of water:

where wherein $R^5$ represents an alkylene group having 3 to 8 carbon atoms.

7. The gel-like composition for a cosmetic preparation according to claim 3, further comprising 1 part by mass to 20 parts by mass of a compound represented by the following formula (2) with respect to 100 parts by mass of water:

wherein $R^5$ represents an alkylene group having 3 to 8 carbon atoms.

8. A cosmetic preparation, comprising the gel-like composition for a cosmetic preparation according to claim 2.

9. A cosmetic preparation, comprising the gel-like composition for a cosmetic preparation according to claim 3.

10. A cosmetic preparation, comprising the gel-like composition for a cosmetic preparation according to claim 4.

* * * * *